United States Patent [19]
Anderson et al.

[11] Patent Number: 5,720,200
[45] Date of Patent: Feb. 24, 1998

[54] PERFORMANCE MEASURING FOOTWEAR

[76] Inventors: Kenneth J. Anderson; Greg D. Anderson, both of 69 S. 1200 East, Lindon, Utah 84042

[21] Appl. No.: 369,641

[22] Filed: Jan. 6, 1995

[51] Int. Cl.$^6$ .................................................. G02M 19/00
[52] U.S. Cl. ...................................... 73/172; 128/779
[58] Field of Search ........................ 73/172, 379.01, 73/379.04; 128/774, 779; 36/1, 114

[56] References Cited

U.S. PATENT DOCUMENTS

| | | | |
|---|---|---|---|
| 3,974,491 | 8/1976 | Sipe | 128/779 X |
| 4,651,446 | 3/1987 | Yukawa et al. | |
| 4,814,661 | 3/1989 | Ratzlaff et al. | |
| 5,269,081 | 12/1993 | Gray | 73/172 X |
| 5,323,650 | 6/1994 | Fullen et al. | 128/779 X |
| 5,357,696 | 10/1994 | Gray et al. | 128/779 X |
| 5,361,778 | 11/1994 | Seitz | 128/779 |
| 5,437,289 | 8/1995 | Liverance et al. | 128/779 |

Primary Examiner—Elizabeth L. Dougherty
Attorney, Agent, or Firm—Thorpe, North & Western, L.L.P.

[57] ABSTRACT

A foot mounted apparatus for measuring one or more locomotive performance parameters of a person is disclosed. Such locomotive performance parameters preferably include user vertical leap time, user vertical jump distance, user walking or running speed, user trip distance traveled, and accumulated total lifetime distance traveled by the apparatus. It is preferred that the apparatus include all of the structures of an athletic shoe such as a sole, upper, tongue, and lace. Four membrane switches are located in the sole of the footwear: a pair of membrane switches is positioned under the ball of the user's foot and a pair of membrane switches is positioned under the heel of the user's foot. The membrane switches sense the compressive pressure of the foot on the sole and detect when the foot leaves and contacts the underlying surface. A microprocessor calculates a performance parameter for the person based upon the elapsed time between the foot push off and the foot strike. A pair of pushbuttons connected to the microprocessor allow the user to change the mode of operation of the apparatus. The performance parameter which is output from the microprocessor is conveyed to the user either visually or aurally. The microprocessor and display are mounted on the footwear, preferably on the tongue of the shoe, in a water resistant housing with a long life battery providing self contained operation.

18 Claims, 3 Drawing Sheets

PERFORMANCE MEASURING FOOTWEAR

BACKGROUND

1. The Field of the Invention

The present invention is related to devices which measure one or more locomotive performance parameters of a person. Such locomotive performance parameters include user vertical leap time, user vertical jump distance, user walking or running speed, user trip distance traveled, and accumulated total lifetime distance traveled by the footwear.

2. The Background Art

Footwear is generally considered an essential item of apparel to most people. In most situations, variability among footwear has primarily focused on its appearance. There exists a multitude of different looks, colors, shapes, and so forth in footwear with relatively few differences in the actual function of the footwear. For most persons, footwear is designed merely for comfort and to get the wearer from here to there. In some instances, the footwear is designed to perform a specific function related to the field of use. Although these aspects are essential to footwear, wearers such as athletes must also have footwear which provides essential functions such as support and cushion.

While many wearers seek desire athletic footwear which promises to improve athletic performance, none of the previously available footwear conveniently and efficiently assists a user in athletic training. Providing a wearer with information such as the distance ran, running speed, distance jumped, and so forth would be very helpful to the wearer.

Efforts to provide a user such information have met with only very limited success in the past. One example of a measuring device placed in footwear for the purpose of measurement of distance traveled is disclosed in U.S. Pat. No. 4,651,446 to Yukawa. The Yukawa reference shows a pedometer linked to footwear. Yukawa placed the pedometer in the insole of the shoe. The insole had a step sensor and sensed the flexing motion of the instep of the footwear so as to provide an output indicative of that motion. The Yukawa device operated through simple counting of flexing of the wearer's foot and created serious discomfort for the user and provided results of questionable accuracy. Most importantly, the Yukawa device only provided a distance traveled function; no other important information is provided to the wearer.

The Yukawa reference also disclosed a pedometer placed outside of a shoe and attached under the shoelace. This prior arrangement makes the display more readable but it exposed the pedometer to damage and excessive wear. The arrangement disclosed in Yukawa of locating the pedometer outside the shoe posed the danger of catching the pedometer on objects in the surrounding environment or receiving a severe, damaging knock. Also, in the prior arrangements, the wearer had to stop exercising to read the display. Disadvantageously, if the wearer must stop the activity to read the display, many wearers would forgo the benefits from such a device. The Yukawa device also was not capable of displaying much of the information which a user finds important.

U.S. Pat. No. 4,814,661 to Ratziaff et al. disclosed a device to measure and analyze forces exerted on a foot to determine what is required to make a shoe more comfortable and/or beneficial to an individual. The Ratziaff et al. device is useful when designing shoes but does not suggest that vertical jump height, the duration of time an individual is suspended in air, or any other locomotive performance parameter should be measured.

In view of the forgoing, it would be an advance in the art to provide footwear which includes devices which are used to measure one or more performance parameters of a user who dons the footwear.

BRIEF SUMMARY AND OBJECTS OF THE INVENTION

In view of the above described state of the art, the present invention seeks to realize the following objects and advantages.

It is a primary object of the present invention to provide a footwear device which provides training information to a user.

It is also an object of the present invention to provide an apparatus for measuring one or more locomotive performance parameter of a user.

It is another object of the present invention to provide footwear which provides information important to the training of the user.

It is yet another object of the present invention to provide a shoe mounted device which can measure locomotive performance parameters of a user such as user vertical leap hang time, user vertical jump distance, user walking or running speed, user trip distance traveled, and accumulated total lifetime distance traveled by the footwear.

It is still another object of the present invention to provide a footwear mounted device which measures one or more locomotive performance parameters of a user which is convenient, efficient, and easy to use.

These and other objects and advantages of the invention will become more fully apparent from the description and claims which follow, or may be learned by the practice of the invention.

The present invention provides a foot mounted apparatus for measuring one or more locomotive performance parameters of a person. Such locomotive performance parameters preferably include user vertical leap time, user vertical jump distance, user walking or running speed, user trip distance traveled, and accumulated total lifetime distance traveled by the embodiment. The invention may be incorporated into many different kinds and types of footwear. It is preferred that the embodiments of the present invention include the structures of an athletic shoe such as a sole, upper, tongue, and lace.

Included in the present invention is a means for sensing the acceleration of the foot when the foot is pushing off from an underlying surface and for generating a foot push off signal. Also included is a means for sensing the deceleration of the foot when the foot is striking against an underlying surface and for generating a foot strike signal. In preferred embodiments, the means for sensing acceleration and deceleration of the user's foot comprises a plurality of membrane switches which are interposed between the user's foot and the underlying surface, preferably within the sole of the footwear. It is also preferred that at least a pair of membrane switches positioned under the ball of the user's foot and at least a pair of membrane switches positioned under the heel of the user's foot be provided. The membrane switches are most preferred for sensing the compressive pressure of the foot on the sole.

Signals are generated by the sensing switches when the user jumps or takes a stride. A means for receiving the foot push off signal and the foot strike signal and means for calculating a performance parameter for the person based upon the elapsed time between the foot push off signal and the foot strike signal is included in the embodiments of the invention. It is preferred that a microprocessor, with appropriate programming and associated circuitry, carry out the functions of receiving the generated signals and performing the necessary calculations. A means for receiving input from the user is provided to allow the user to provide input to the microprocessor. The means for receiving input preferably comprises a pair of pushbuttons connected to the microprocessor.

Signals which are output from the means for calculating are conveyed to a means for communicating at least one performance parameter to the user. The means for communicating can preferably include: a means for visually conveying the at least one performance parameter to the person mounted on the foot; means for transmitting a broadcast signal from a location adjacent to the means for calculating and an accompanying means for visually conveying the at least one performance parameter to the person in a location distant from the means for transmitting; means for providing audible cues from the calculation means to the user; and, means for synthesizing human speech and translating the at least first performance parameter into human speech.

The calculation and a display device are preferably mounted on the footwear, most preferably on the tongue of a shoe, in a water resistant housing. A long life battery is also included to allow self contained operation.

The method of the present invention determines at least one performance parameter of a user. The method includes the step of detecting when at least one of the user's feet leaves an underlying surface during a locomotion by the user and the step of timing a period beginning when at least one foot leaves the underlying surface is detected. The step of detecting when at least one of the user's feet strikes the underlying surface during a locomotion by the user is also included. A time period between when at least one foot leaves the underlying surface and when at least one foot strikes the underlying surface is derived and at least one performance parameter for the user is calculated based upon this time period. The performance parameter is preferably at least one selected from the group of performance parameters comprising: user vertical leap time and user vertical jump distance and more preferably including user running speed, user trip distance traveled, and accumulated total lifetime distance traveled by the apparatus. The performance parameter is then displayed on a visually perceptible display or conveyed to the user in some other manner.

BRIEF DESCRIPTION OF THE DRAWINGS

In order to better appreciate how the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered limiting of its scope, the invention will be described and explained with additional specificity and detail through the use of the accompanying drawings in which.

DETAILED DESCRIPTION OF THE PREFERRED EMBODIMENTS

Reference will now be made to the drawings wherein like structures will be provided with like reference designations.

The present invention measures and provides one or more locomotive performance parameters for a user. Such locomotive performance parameters include: 1) the vertical leap hang time of the user; 2) the vertical jump distance of the user; 3) the walking or running speed of the user; 4) the user trip distance traveled; and, 5) the accumulated total lifetime distance traveled by the footwear. The present invention benefits users with a wide range of abilities and lifestyles, for example, both professional athletes and occasional walkers can benefit from the present invention. Users of all ages can benefit from the present invention by having numerous performance parameters automatically, conveniently, and accurately measured which has not been available prior to the present invention.

As will be appreciated from an understanding of the teachings contained herein, the present invention utilizes forces and actions imposed by the user's foot during walking, running, and jumping activities of the user in order to determine the performance parameters.

Preferred embodiments of the present invention can be incorporated into many different types of footwear. For example, the preferred embodiment of the invention described herein includes the structures conventionally found in an athletic shoe, as can be readily devised by those skilled in the pertinent art.

Figure 1A:
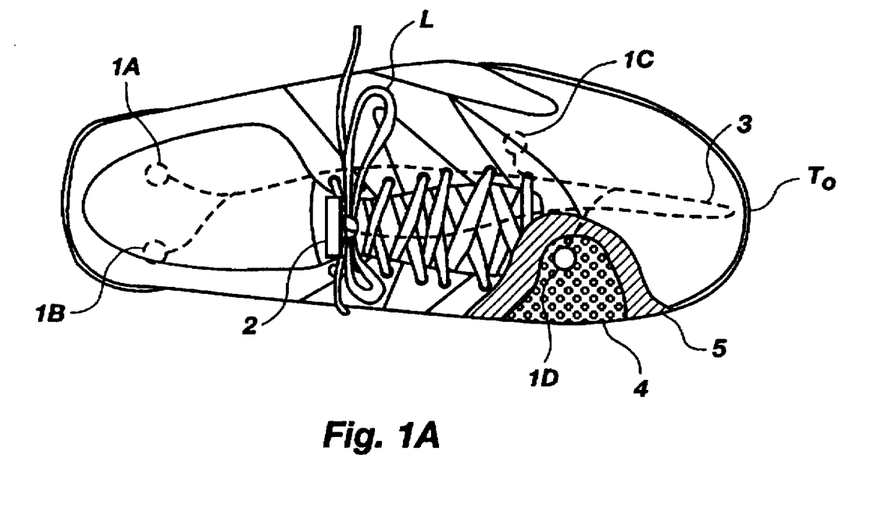
FIG. 1A is a partially cut away top view a first embodiment of the present invention.
Figure 1B:
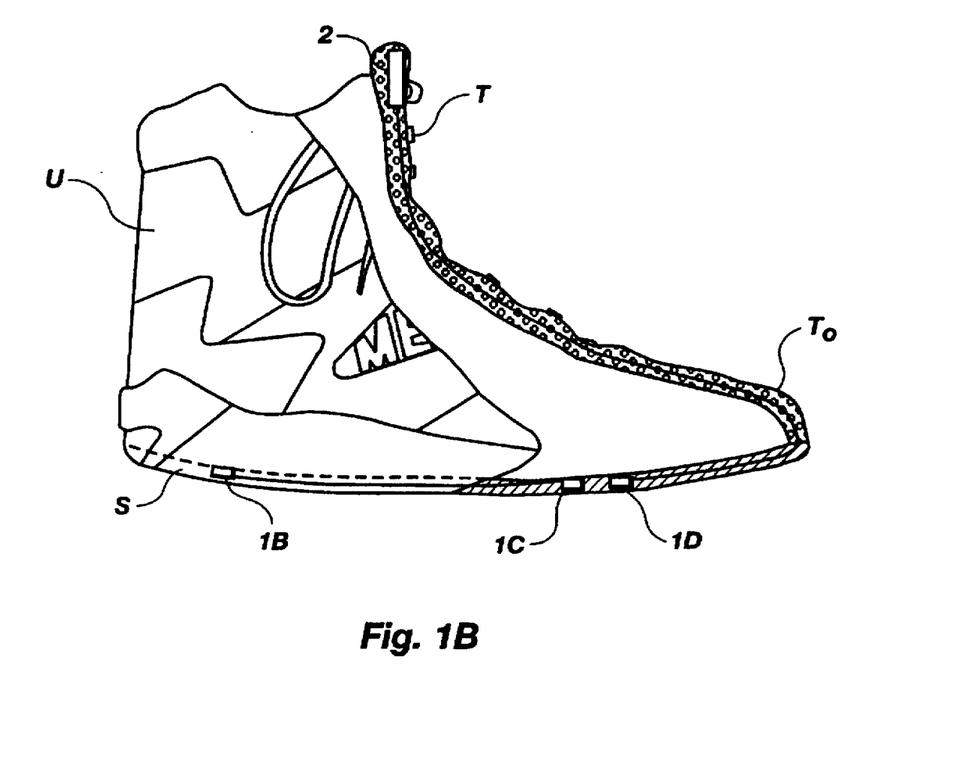
FIG. 1B is a partially cut away side view of the embodiment illustrated in FIG. 1A.
Figure 1C:
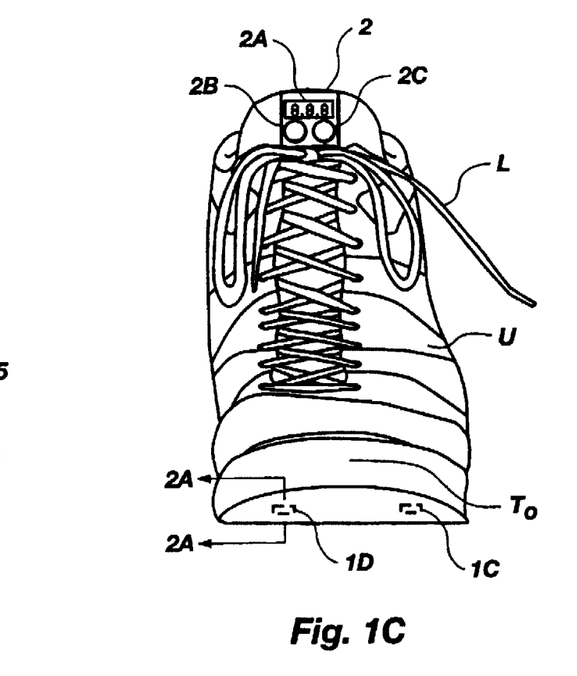
FIG. 1C is a front view of the embodiment illustrated in FIG. 1A.

Reference will first be made to FIGS. 1A, 1B, and 1C, which are top, side, and front views, respectively, of the presently preferred embodiment of the present invention. As seen in FIGS. 1A–C, the preferred embodiment is an athletic shoe including a sole S, and upper U, a tongue T and a lace L. It will be appreciated that the illustrations provided in FIGS. 1A–C are not necessarily to any scale and that the present invention may be incorporated into many different kinds and types of footwear, including sandals and boots of many kinds.

Figure 2:
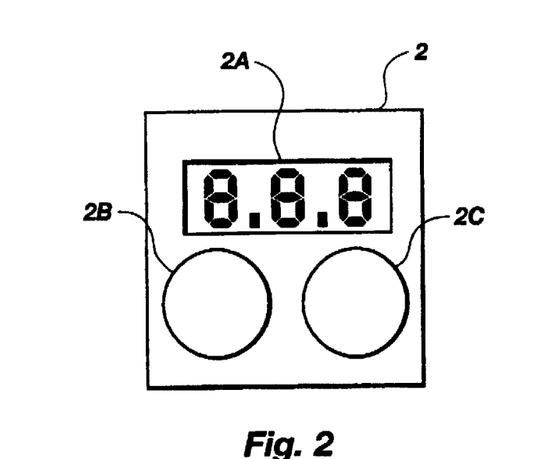
FIG. 2 is a detailed view of the calculation and display unit illustrated in FIGS. 1A–C.

Represented best in FIGS. 1C and 2, a calculation and display unit 2 preferably performs many of the functions of the present invention. Included in the calculation and display unit 2 are two operating pushbuttons 2B and 2C (which function as user input devices) and a display 2A. As will be explained shortly, the calculation and display unit 2 also preferably includes a central processing unit (CPU)(10 in FIG. 3), a battery (16 in FIG. 3), and a piezoelectric speaker (14 in FIG. 3) as well as other components which will be described later. The components of the calculation and display unit 2 are desirably encased in a water-proof plastic enclosure that is permanently attached to the upper tongue T of the footwear.

As can be seen in FIGS. 1A–C, the sole S can be of conventional construction with modifications to accommodate the components required to carry out the invention. Membrane switches, four of which are indicated at 1A–D, are positioned in four different locations of the sole S. The membrane switches 1A–D are preferably normally open switches but other configurations can also be used within the scope of the present invention. As represented best in FIG.

1A, two membrane switches 1A–B are positioned under the heel of the user and two membrane switches 1C–D under the ball of the foot of the user.

Those skilled in the pertinent arts will readily understand the anatomical structures defined by the terms "heel" and "ball of the foot" and the corresponding portions of the sole S which are referred to even though the user's foot has not been pictured in order to increase the clarity of the figures. As illustrated best in FIG. 1A, a wiring connection 3, preferably a thick film flex membrane connection with three conductors, functions to make connections to the switches 1A–D. The wiring connection 3 is routed along the length of the sole S, up through a toe $T_o$ of the footwear, and along the length of the tongue T to the calculation and display unit 2.

It is preferred that the membrane switches 1A–B located at the heel be wired in parallel such that when either of the two switches closes the calculation and display unit 2 will receive a signal. Similarly, the membrane switches 1C–D located at the ball of the foot are preferably wired in parallel such that when either of the two switches closes the calculation unit will receive a signal. This preferred arrangement of switches 1A–D accommodates different footfalls and walking/running patterns.

The membrane switches 1A–D are preferably sealed and are closed when a compressive force is applied to sides of the switches 1A–D. The closure action is transmitted to the calculation and display unit 2 through the de-bounce circuit 9 so that the membrane switch closing or opening is verified and can be relied upon to represent a valid switch action. With each closing of a switch, the CPU 10 then determines from the validated switch action and the selected mode, which has been pre-determined by the user, whether to start or stop the current operation during the vertical leap measurement, or to count an additional stride and accumulate the additional distance into internal memory during the distance measurement operation. The CPU 10 also updates the display to show the vertical leap time, vertical leap distance or updates the display to show the additional distance traveled.

It will be appreciated that the membrane switches 1A–D are selected so that the expected compressive force will close the switches. In the case of an embodiment of the invention used in children's footwear, the switches can be selected to close with less force than switches incorporated into adult footwear. Those skilled in the art will appreciate that while the described membrane switches are preferred, other structures which detect the acceleration and deceleration of the user's foot can also be used within the scope of the present invention. The specified membrane switches 1A–D are merely exemplary of the various devices which can be used to detect compressive forces exerted by a user's foot and the acceleration and deceleration forces experienced by the user's foot.

It is preferred that the sole S include at least two layers, as indicated at 4 and 5 in FIG. 1A, which can be selected by those skilled in the pertinent art using the information set forth herein and which will allow proper operation of the membrane switches 1A–D.

Figure 2A:
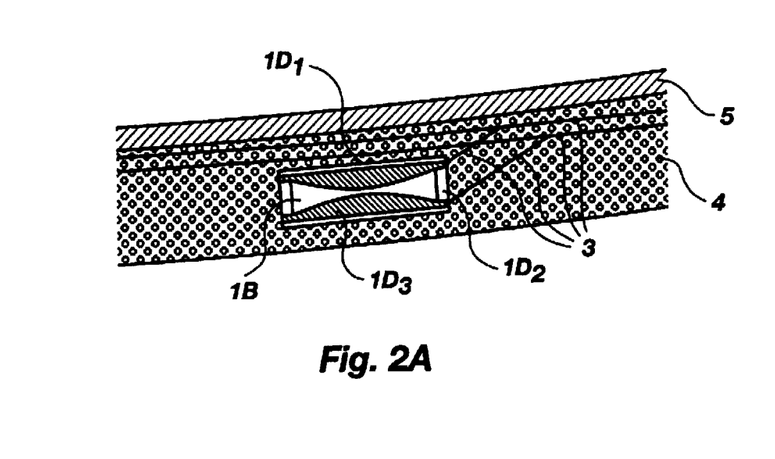
FIG. 2A is a detailed cross sectional view taken along line 2A—2A of FIG. 1C.

The construction of the membrane switches 1A–D can be seen best in the cross sectional view of FIG. 2A. The membrane switch 1D represented in FIG. 2A is constructed of flexible insulating outer panels $1D_1$ molded together with insulating spacers $1D_2$ with conductive membranes $1D_3$ in close proximity to each other at a rest position. When a compressive force is applied to the sole S by the user, indicating acceleration or deceleration of the user's foot, the two conductive membranes $1D_3$ are forced together making contact with each other and completing an electrical circuit and indicating closure of the switch to the calculation and display unit 2.

In FIG. 1C the calculation and display unit 2 is shown mounted onto the tongue T. Mounting the calculation and display unit 2 in the tongue T is preferred to provide convenient access for the user. It will be appreciated that the calculation and display unit 2 can be mounted in other locations within the scope of the present invention. In the detailed view of FIG. 2, the display 2A and two pushbuttons 2B and 2C are represented.

Figure 3:
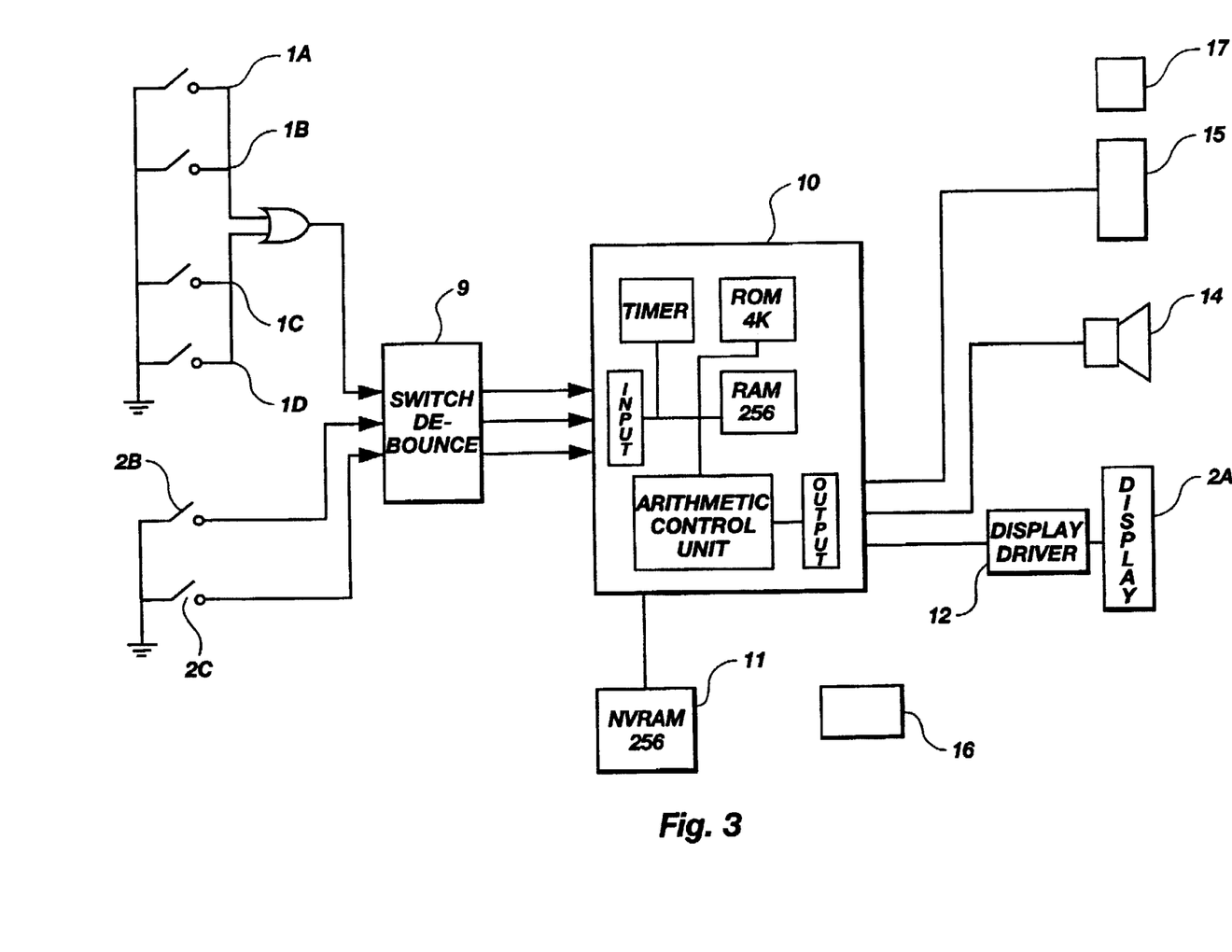
FIG. 3 is block diagram showing the preferred arrangement of the electrical components included in the embodiment illustrated in FIGS. 1A–C and 2–2A.

Reference will next be made to FIG. 3 which is a block diagram showing the preferred electrical and electronic components. Represented in FIG. 3 are the four membrane switches 1A–D which are positioned in the sole S as illustrated in FIGS. 1A–C. Pairs of the membrane switches 1A–B and 1C–D are OR'ed together to each provide a single input into a CPU 10 through a de-bounce circuit 9 to prevent false triggering during slight movements by the user. The outputs from a Reset/Start pushbutton 2B and the Function/Select 2C pushbutton are also sent through the de-bounce circuit 9. The respective outputs from the de-bounce circuit 9 are fed into the self-contained CPU 10 where they are used to calculate values which are output and displayed. As will be explained shortly, the CPU includes a Read-Only-Memory (ROM) section which contains instructions for the CPU to carry out the various measuring functions as herein explained. The CPU 10 also includes a real time clock/timer which is used to accurately calculate locomotive performance parameters for the user.

It is preferred that the CPU 10 be a microprocessor designated in the industry as HMCS47CL. Other microprocessors, as well as other components, can be used to carry out the functions described herein within the scope of the present invention. Required data is stored within a Non-Volatile Read-Only-Memory (NVRAM) 11, such as to allow the accumulation of distance for the lifetime of the embodiment. The NVRAM is preferably one designated in the art as X24022 but those skilled in the art can select other equivalent components to carry out the functions of the NVRAM using the information contained herein. If necessary, programming code can also be stored in a memory external to the CPU 10.

It is preferred that the embodiment automatically power-down when not being used to conserve the battery 16. The battery 16 is preferably a lithium battery or other long life battery or cell. It is also within the scope of the present invention to use rechargeable batteries with an external charger (not illustrated in the figures) or accommodation can be made to replace the battery 16.

The CPU 10 carries out programming instructions which can be arrived at by those skilled in the art using the information contained herein. The CPU 10 outputs information to various devices to suit the needs of the user as will be discussed shortly. In the preferred default mode, the CPU 10 outputs information through a display driver 12 to the display 2A. The display driver 12 is preferably an integrated circuit designated in the industry as HD44102CH but those skilled in the art will be able to chose other components which carry out equivalent functions. The display 2A is preferably a 440×218 dot matrix LCD display. The display 2A is just one of a number of different output devices which can be used within the scope of the present invention. All of the output devices which are selected preferably should be selected for their low power consumption and robust characteristics.

Also preferably included is a speaker 14 to provide operating cues and prompts to the user. Preferably accompanying the speaker is a speech synthesis unit which allows the speaker to output verbal information to the user. The inclusion of a speech synthesis feature allows the present invention to be more conveniently used by a wider segment of the population, including visually handicapped users. By selection of an appropriate CPU 10 and programming code using information known in the art and set forth herein, speech synthesis can be readily implemented in embodiments of the present invention.

Also represented in the embodiment of FIG. 3 is a wireless transmitter 15. The wireless transmitter 15 utilizes infrared or radio frequency modulation techniques, both known in the art, to transmit information from the calculation and display unit to a remote receiver 17 which can be located on the body of the user, such as a wrist mounted display, ear mounted speaker, or a projection display onto an eye shield (not represented in the figures) as can be devised using information available in the art. The wireless transmitter 15 can also transmit information to a remote receiver located, for example, at the position of a coach, trainer, or other person advising the user. It is also within the scope of the present invention to transmit information to an information recording and analyzing device, such as a personal computer.

It will be appreciated that the above described components which are positioned on the user or the user's footwear are preferably sealed into a module(s) for ease of manufacturing and durability during use.

The embodiment represented in the figures determines and reports to the user several different useful performance parameters. It is preferred that the illustrated embodiment provide to the user the following locomotive performance parameters, each of which will shortly be discussed below in greater detail: user vertical leap time, user vertical jump distance, user walking or running speed, user trip distance traveled, and accumulated total lifetime distance traveled by the embodiment. As will be appreciated from the following discussion, each performance parameter is derived from the input of the membrane switches 1A–D but a different parameter is conveyed to the user on the display 2A in accordance with a different sequence of pushbuttons 2B–C which are actuated by the user.

It is preferred that the accumulated total lifetime distance traveled by the embodiment be the default mode which is displayed when no other parameter is being displayed. It will be appreciated that the distance can be displayed in miles or any other unit of measurement which is desired.

To measure user vertical jump distance, the user actuates both pushbuttons 2B–C simultaneously for two seconds to place the calculation and display unit 2 into a function select mode. With the calculation and display unit 2 in the function select mode, the function/select pushbutton 2C is actuated until the display 2A prompts "Vert/Dist." The embodiment is ready to measure the vertical jump distance of the user. The calculation and display unit 2 preferably waits for the heel membrane switches 1C–D and the ball of the foot membrane switches 1A–B to open, indicating that the sole S has left contact with the underlying surface, at which time the CPU begins a timing operation. If the user does not jump, i.e., all of the membrane switches do not open, for one minute the calculation and display unit 2 returns to its default mode showing the accumulated total lifetime distance. After the embodiment enters the vertical jump distance mode, when the user's foot leaves the underlying surface, i.e., the sole S leaves the underlying surface, all of the membrane switches 1A–D are open and the CPU 10 begins to clock the time that elapses until one or more of the membrane switches 1A–D again return to their normally closed position caused by some portion of the user's foot and the sole S striking the underlying surface and causing the rapid deceleration of the user's foot.

From the time determined by the CPU 10, the CPU 10 calculates the vertical distance that the user reached based upon the earth's gravitational constant. It is preferred that the display 2A show the calculated vertical distance for about one minute or until the function/select pushbutton is used to restart the "Vert/Dist" measurement again.

While the positions of the membrane switches 1A–D illustrated in FIG. 1A–C are presently preferred, it will be understood that additional membrane switches can be positioned under different portions of the user's foot, if desired, or the positions indicated in the figures may be altered.

To measure the user vertical jump hang time, the user pushes both of the buttons simultaneously for two seconds to place the unit into its function mode. The function button is then repeatedly pushed until the display reads "Vert/Time" indicating that the embodiment is now ready to measure and display the users vertical leap time. After the control/display unit 2 is set, the user's foot must leave the ground within one minute for the timing function to begin before it returns to the default distance accumulation mode. Once the sole S leaves the ground, the CPU 10 accurately measures the time until one or any combination of the switches are closed. The user's hang time is then shown on the display 2A for a period of time long enough to allow the user to note the same.

To measure the user's speed, either when walking or running, the CPU 10 counts each occurrence that the membrane switches 1A–D open and close which indicates that the user has taken a full stride. Using the information set forth herein, those skilled in the pertinent art can derive appropriate algorithms which can be carried out and used by the CPU to improve the accuracy the calculations made by the CPU 10.

It will be appreciated that the length of the user's stride is a variable which must be supplied to the CPU 10. Prior to beginning operation, the user enters a stride length into the calculation and display unit 2 during a calibration procedure. The user can derive a stride length by taking appropriate strides on an accurately marked course while counting the number of strides taken for course. The distance traveled over the course is then divided by the number of strides taken and the length of the stride is converted into inches. The user then actuates both pushbuttons 2B and 2C for five seconds which places the calculation and display unit 2 into a set/calibrate mode. The user then repeatedly pushes the function/select pushbutton 2C to increment the stride length (displayed in inches on the display 2A) or the reset/start pushbutton to decrement the stride length until the desired stride length is displayed. When the desired stride length is displayed, both pushbuttons 2B and 2C are again pushed for one second and the stride length is stored into the NVRAM 11 for use.

After the stride calibration procedure has been completed, the user can actuate both pushbuttons 2B and 2C simultaneously for two seconds to place the calculation and display unit 2 in the distance measure mode. The user then actuates the function/select pushbutton 2C until "Dist" appears on the display 2A indicating that the distance mode has been entered. To clear the distance display and reset the distance display to zero, the user actuates the reset/start pushbutton 2B while in the distance mode and holds both pushbuttons 2B for two seconds. After the display 2A clears, the user then can begin walking or running and the display will be periodically updated with the distance which has been traveled as calculated by the calculation and display unit 2. The display 2A will continue show the updated distance until the reset/start pushbutton 2B is actuated for less than two seconds which will stop the display until the reset/start pushbutton 2B is actuated again. In this way a rest period can be taken by the user and the calculation and display unit 2 will not count strides taken by the user. To resume with counting of strides, the user pushes the reset/start pushbutton 2B again and the calculation and display unit will again count strides and update the display 2A from the distance previously indicated.

To enter the speed measurement mode of the calculation and display unit 2, the user actuates the function/select pushbutton 2C anytime that the calculation and display unit 2 is in the distance measure mode. Upon entering the speed measurement mode, the display 2A is changed to show the user's linear travel speed which will be periodically updated. It will be appreciated that accurate calibration of the stride length into the calculation and display unit 2 is important to obtaining accurate results with the embodiments of the present invention. It will also be appreciated that those skilled in the art can arrive at the necessary programming to allow multiple stride lengths to be entered during the calibration procedure so that the most precise stride length can be used in accordance with whether the user is walking, jogging, or running. It is also within the scope of the present invention to provide programming which will automatically select one of a plurality of stride lengths which have been previously entered by the user in accordance with the activity the user is engaged in, for example, walking or running.

The calculation and display unit 2 continues to record distance information to provide an accumulated total lifetime distance. To display the accumulated total lifetime distance on the display 2A, the user actuates both pushbuttons 2B and 2C in order to enter the function mode and then actuates the function/select pushbutton 2C until "Life" is shown in the display 2A. The display 2A will then indicate the total distance corresponding to the strides counted since the calibration procedure was last completed.

It will be appreciated that the present invention provides an apparatus and method for efficiently and conveniently providing training information to a user which can be incorporated into different types of footwear. The embodiments of the present invention efficiently measures one or more locomotive performance parameter of a user, such as vertical jump height, vertical jump hang time, and the speed of the user as the user walks, jogs, or runs as well as the distance traveled by the user.

The present invention may be embodied in other specific forms without departing from its spirit or essential characteristics. The described embodiment is to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A foot mounted apparatus for measuring the locomotive performance of a person having a foot which is fit with footwear having a flexible sole, the apparatus comprising:

means for sensing the acceleration of the foot when the sole of the footwear is flexed and the foot is pushing off from an underlying surface and for generating a foot push off signal;

means for sensing the deceleration of the foot when the foot is striking against an underlying surface and for generating a foot strike signal;

means for receiving the foot push off signal and the foot strike signal and calculating a performance parameter for the person based upon the elapsed time between the foot push off signal and the foot strike signal, the means for calculating comprising means for selectively determining all of the following performance parameters: user vertical leap time, user vertical jump distance, user running speed, user trip distance traveled, and accumulated total lifetime distance traveled by the apparatus;

means for receiving input from the user, and means for communicating at least one performance parameter to the person.

2. An apparatus as defined in claim 1 wherein the means for communicating comprises means for visually conveying the at least one performance parameter to the person mounted on the foot.

3. An apparatus as defined in claim 1 wherein the means for visually conveying comprises at least one LCD display.

4. An apparatus as defined in claim 1 further comprising a flexible sole, and a tongue.

5. An apparatus as defined in claim 4 further comprising an upper, a tongue, and a lace.

6. An apparatus as defined in claim 1 wherein the means for sensing the acceleration comprises at least a first switch positioned under the ball of the user's foot and at least a second switch positioned under the heel of the user's foot.

7. An apparatus as defined in claim 6 wherein the means for sensing the acceleration further comprises a third switch positioned under the ball of the user's foot, the first switch and the third switch both being positioned in the sole.

8. An apparatus as defined in claim 7 wherein the means for sensing the deceleration further comprises a fourth switch positioned under the user's foot, the second switch and the fourth switch both being positioned in the sole.

9. An apparatus as defined in claim 1 wherein the means for calculating comprises a microprocessor.

10. An apparatus for measuring the locomotive performance of a user having a foot with a heel and a ball, the apparatus comprising:

a sole, the sole being flexible and configured to be interposed between both the heel of the foot of the user and the ball of the foot of the user and any underlying surface;

first switch means attached to the sole in the location of the user's heel for sensing compressive pressure of the foot on the sole;

second switch means attached to the sole in the location of the user's ball of the foot for sensing compressive pressure of the foot on the sole;

calculation means for determining the time between the activation of the first switch means and the second switch means and for calculating at least a first locomotive performance parameter for the user, the first locomotive performance parameter being selected from the group consisting of: user vertical leap time, user vertical jump distance, user running speed, user trip distance traveled, and accumulated total lifetime distance traveled by the apparatus;

means for providing audible cues from the calculation means to the user;

means for receiving tactile input from the user and converting such input to instructions conveyed to the calculation means; and alpha/numeric display means for visually displaying the at least one performance parameter.

11. An apparatus as defined in claim 10 wherein the first switch means comprises at least two membrane switches and wherein the second switch means comprises at least two membrane switches.

12. An apparatus as defined in claim 11 further comprising:

an upper attached to the sole;

a tongue attached to the upper;

a lace connected to the upper;

wherein the calculation means comprises a microprocessor;

wherein the display means comprises a LCD display; and wherein the means for receiving tactile input comprises at least a pair of pushbuttons.

13. An apparatus as defined in claim 12 further comprising:

means for transmitting a broadcast signal from a location adjacent to the calculation means; and means for visually conveying the at least one performance parameter to the person in a location distant from the means for transmitting.

14. A method for determining at least one performance parameter of a user having a pair of feet, each of the feet being fit with footwear having a flexible sole, the method comprising:

receiving input from the user regarding at least one performance parameter;

detecting when at least one of the feet leaves an underlying surface as the sole of the footwear is flexed during a locomotion by the user;

timing a period beginning when the at least one foot leaves the underlying surface is detected;

detecting when at least one of the feet strikes the underlying surface during a locomotion by the user;

deriving a time period between when the at least one foot leaving the underlying surface and when the at least one foot striking the underlying surface;

calculating at least one performance parameter for the user, the performance parameter being at least one selected from the group of performance parameters comprising: user vertical leap time and user vertical jump distance; and displaying the at least one performance parameter on a visually perceptible display.

15. A method as defined in claim 14 wherein the group of performance parameters further comprises: user running speed, user trip distance traveled, and accumulated total lifetime distance traveled by the apparatus.

16. A method as defined in claim 14 wherein the step of detecting when at least one of the feet leaves an underlying surface comprises the detection of the closing of at least one switch interposed between the at least one of the user's feet and the underlying surface.

17. A foot mounted apparatus for measuring the locomotive performance of a person, the apparatus comprising:

means for sensing the acceleration of the foot when the foot is pushing off from an underlying surface and for generating a foot push off signal;

means for sensing the deceleration of the foot when the foot is striking against an underlying surface and for generating a foot strike signal;

means for receiving the foot push off signal and the foot strike signal and calculating a performance parameter for the person based upon the elapsed time between the foot push off signal and the foot strike signal; and means for communicating at least one performance parameter to the person, the means for communicating comprising:

means for transmitting a broadcast signal from a location adjacent to the means for calculating; and means for visually conveying the at least one performance parameter to the person in a location distant from the means for transmitting.

18. A foot mounted apparatus for measuring the locomotive performance of a person, the apparatus comprising:

means for sensing the acceleration of the foot when the foot is pushing off from an underlying surface and for generating a foot push off signal;

means for sensing the deceleration of the foot when the foot is striking against an underlying surface and for generating a foot strike signal;

means for receiving the foot push off signal and the foot strike signal and calculating a performance parameter for the person based upon the elapsed time between the foot push off signal and the foot strike signal; and means for communicating at least one performance parameter to the person, the means for communicating comprising means for synthesizing human speech and translating the at least first performance parameter into human speech.

* * * * *

EX PARTE REEXAMINATION CERTIFICATE (10355th)

United States Patent
Anderson et al.

(10) Number: US 5,720,200 C1
(45) Certificate Issued: Oct. 23, 2014

(54) PERFORMANCE MEASURING FOOTWEAR

(75) Inventors: Kenneth J. Anderson, East Lindon, UT (US); Greg D. Anderson, East Lindon, UT (US)

(73) Assignee: Icon Health & Fitness, Inc., Logan, UT (US)

Reexamination Request:
No. 90/013,075, Dec. 4, 2013

Reexamination Certificate for:
Patent No.: 5,720,200
Issued: Feb. 24, 1998
Appl. No.: 08/369,641
Filed: Jan. 6, 1995

(51) Int. Cl.
*A61B 5/11* (2006.01)

(52) U.S. Cl.
CPC ..................................... *A61B 5/112* (2013.01)
USPC .................... 73/172; 702/41; 36/114; 36/132; 36/137

(58) Field of Classification Search
None
See application file for complete search history.

(56) References Cited

To view the complete listing of prior art documents cited during the proceeding for Reexamination Control Number 90/013,075, please refer to the USPTO's public Patent Application Information Retrieval (PAIR) system under the Display References tab.

*Primary Examiner* — Dennis Bonshock (57) ABSTRACT

A foot mounted apparatus for measuring one or more locomotive performance parameters of a person is disclosed. Such locomotive performance parameters preferably include user vertical leap time, user vertical jump distance, user walking or running speed, user trip distance traveled, and accumulated total lifetime distance traveled by the apparatus. It is preferred that the apparatus include all of the structures of an athletic shoe such as a sole, upper, tongue, and lace. Four membrane switches are located in the sole of the footwear: a pair of membrane switches is positioned under the ball of the user's foot and a pair of membrane switches is positioned under the heel of the user's foot. The membrane switches sense the compressive pressure of the foot on the sole and detect when the foot leaves and contacts the underlying surface. A microprocessor calculates a performance parameter for the person based upon the elapsed time between the foot push off and the foot strike. A pair of pushbuttons connected to the microprocessor allow the user to change the mode of operation of the apparatus. The performance parameter which is output from the microprocessor is conveyed to the user either visually or aurally. The microprocessor and display are mounted on the footwear, preferably on the tongue of the shoe, in a water resistant housing with a long life battery providing self contained operation.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 1-9 and 17 is confirmed.

Claims 14 and 15 are cancelled.

Claims 10-13, 16 and 18 were not reexamined.

\* \* \* \* \*